US00PP10663P

United States Patent [19]

VandenBerg

[11] Patent Number: Plant 10,663

[45] Date of Patent: Oct. 27, 1998

[54] CHRYSANTHENUM PLANT NAMED 'DETROIT'

[75] Inventor: Cornelis P. VandenBerg, Salinas, Calif.

[73] Assignee: Yoder Brothers, Inc., Barberton, Ohio

[21] Appl. No.: 786,422

[22] Filed: Jan. 21, 1997

[51] Int. Cl.[6] ..... A01H 5/00

[52] U.S. Cl. ..... Plt./82.5

[58] Field of Search ..... Plt./74.1, 82.5

[56] References Cited

PUBLICATIONS

UPOV–ROM, Apr. 1997, Plant Variety Database, GTI Jouve Retrieval Software, 3 citations for 'Detroit'.

*Primary Examiner*—Howard J. Locker
*Attorney, Agent, or Firm*—Foley & Lardner

[57] ABSTRACT

A Chrysanthemum plant named Detroit particularly characterized by its flat captiulm form; daisy capitulum type; red ray floret color with a green disc and a small brown dot in the center of the disc; diameter across face of captilum of 73 to 76 mm when fully opened; flowering response in Salinas under normal tempeatures is 53 to 56 days after start of short days; plant height is 89 to 109 cm when grown in Salinas with 11 to 17 long days prior to start of short days; penduncle length of the first and the fourth laterals at flowering after removing the apical bud is 8 to 13 cm and 20 cm when grown in Salinas, Calif.; production of 9 to 13 laterals, each producing one terminal flower when grown in Salinas, Calif.; and uniform flowering in year round flowering.

3 Drawing Sheets

The present invention comprises of a new and distinct cultivar of Chrysanthemum, botanically known as *Dendranthema grandiflora,* and referred to by the cultivar name Detroit.

Detroit, identified as B867 (92-721003), was originated from a cross made by Cornelis P. VandenBerg in a controlled breeding program in Salinas, Calif., in 1991.

The female parent of Detroit was the cultivar Foxy, disclosed in U.S. Plant Patent No. 5,414 , and described as a flat daisy spray cut mum with red ray floret color.

The male parent of Detroit was an unnnamed seedling, identified as 0617 (87-826002) and described as a flat daisy spray cut mum with dark red ray floret color. The male was discarded from all programs in May 1997.

Detroit was discovered and selected as one flowering plant within the progeny of the stated cross by Cornelis P. VandenBerg in January 1993, in a controlled environment in Alva, Fla.

The first act of asexual reproduction of Detroit was accomplished when vegetative cuttings were taken from the initial selection in March of 1993 in a controlled environment in Alva, Fla., by technicians working under supervision of Cornelis P. VandenBerg.

Horticultural examination of controlled flowerings of successive plantings has shown that the unique combination of characteristics as herein disclosed for Detroit are firmly fixed and are retained through successive generations of asexual reproduction. Detroit has not been observed under all possible environmental conditions. The phenoytpe may vary significantly with variations in environment such as temperature, ligh intensity and daylength, without, however, any variance in genotype.

The following observations, measurements and comparisons describe plants grown in Salinas, Calif. under greenhouse conditions which approximate those generally used in commercial greenhouse practice.

The following traits have been repeatedly observed and are determined to be basic characteristics of Detroit, which, in combination, distinguish this Chrysanthemum as a new and distinct cultivar:

1. Flat captiulum form.
2. Daisy capitulum type.
3. Red ray floret color with a green disc and a small brown dot in the center of the disc.
4. Diameter across face of capitulm of 73 to 76 mm when fully opened.
5. Flowering response in Salinas under normal temperatures is 53 to 56 days after start of short days.
6. Plant height is 89 to 109 cm when grown in Salinas with 11 to 17 long days prior to start of short days.
7. Peduncle length of the first and the fourth laterals at flowering after removing the apical bud is 8 to 13 cm and 13 to 20 cm when grown in Salinas, Calif.
8. Production of 9 to 13 laterals, each producing one terminal flower when grown in Salinas, Calif.
9. Uniform flowering in year round flowerings.

The accompanying photographic drawings show typical inflorescence and leaf characteristics of Detroit, with the colors being as nearly true as possible with illustrations of this type.

Sheet 1 is a color photograph of Detroit grown as a single stem spray cut mum.

Sheet 2 is a black and white photograph of three views of the inflorescence of Detroit.

Sheet 3 is a black and white photograph showing the upper and under sides of the leaves of Detroit at 3 stages of development (mature, intermediate and immature). In sheets 2 and 3 a measuring tape in centimeters has been added.

Of the commerical cultivars known to the inventor, the most similar in comparison to Detroit is the female parent cultivar Foxy. Reference is made to attached Chart A, which compares certain characeristics of Detroit with the same characteristics of Foxy. Similar traits are ray floret color, capitulum form and type, and plant height. Peduncle length of both cultivars is comparable. Detroit has a slightly smaller diameter of capitulum and a faster flowering response by 1 to 3 days when compared with Foxy. In addition, Detroit has a distinct brown dot in the center of the disc, while Foxy does not exhibit this distinct dot.

In the following description color references are made to The Royal Horticultural Society Colour Chart. The color values were determined on plant material grown as a single stem spray cut mum in Salinas, Calif. on Jun. 13, 1996.

Classification:

*Botanical.*—*Dendranthema grandiflora* cv Detroit.

*Commercial.*—Flat daisy sprat cut mum.

Inflorescence

A. Capitulum:

*Form.*—Flat.

*Type.*—Daisy.

*Diameter across face.*—73 to 76 mm when fully opened.

Corolla of ray florets:

*Color.*—(*general tonality from a distance of three meters*) —Red.

*Color.* (*upper surface*): 46A. *Color* (*under surface*).—Closet to 180C. *Shape.*—Cross section flat, longitudinal section of outer ray florets straight, ray floret tip rounded.

Corolla of disc florets:

*Color* (*mature*).—Closet ot 154A.

*Color* (*immature*).—Closest to 144A. Distinct small brown (RHS 166A) center of corolla of disc florets.

Reproductive organs:

*Androecium.*—Present on disc florets only; no pollen.

*Gynoecium.*—Present on both ray and disc florets.

Plant

A. General appearance:

*Height.*—89 to 109 cm when grown in Salinas with 11 to 17 long days prior to start of short days.

Foliage:

*Color* (*upper surface*).—147A. *Color* (*under surface*).—147B. *Shape.*—Deeply lobed, strongly serrated.

CHART A

COMPARISONS MADE OF PLANTS GROWN AS SINGLE STEM SPRAY CUT MUMS IN SALINAS, CALIFORNIA

| CHARACTERISTIC | DETROIT | FOXY |
|---|---|---|
| Ray floret color | Red | Red |
| Capitulum form and type | Flat daisy | Flat daisy |
| Diameter across face of capitulum | 73 to 76 mm | 73 to 85 mm |
| Flowering response | 53 to 56 days | 54 to 59 days |
| Plant height | 89 to 109 cm | 89 to 109 cm |
| Peduncle length | | |
| 1st lateral | 8 to 13 cm | 8 to 10 cm |
| 4th lateral | 13 to 20 cm | 13 to 20 cm |

What is claimed is:

1. A new and distinct Chrysanthemum plant named Detroit, as described and illustrated.

* * * * *

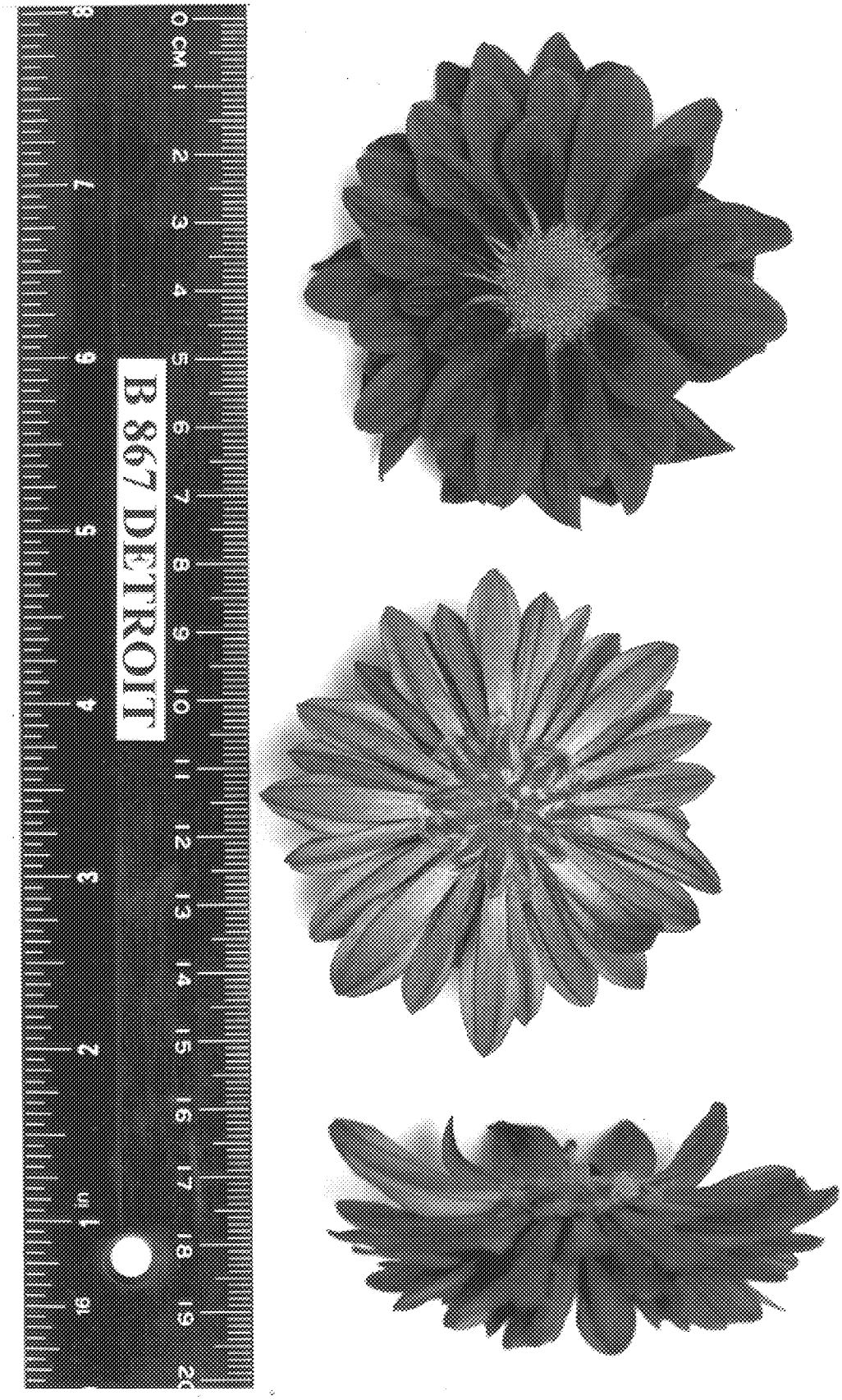
B 867 DETROIT

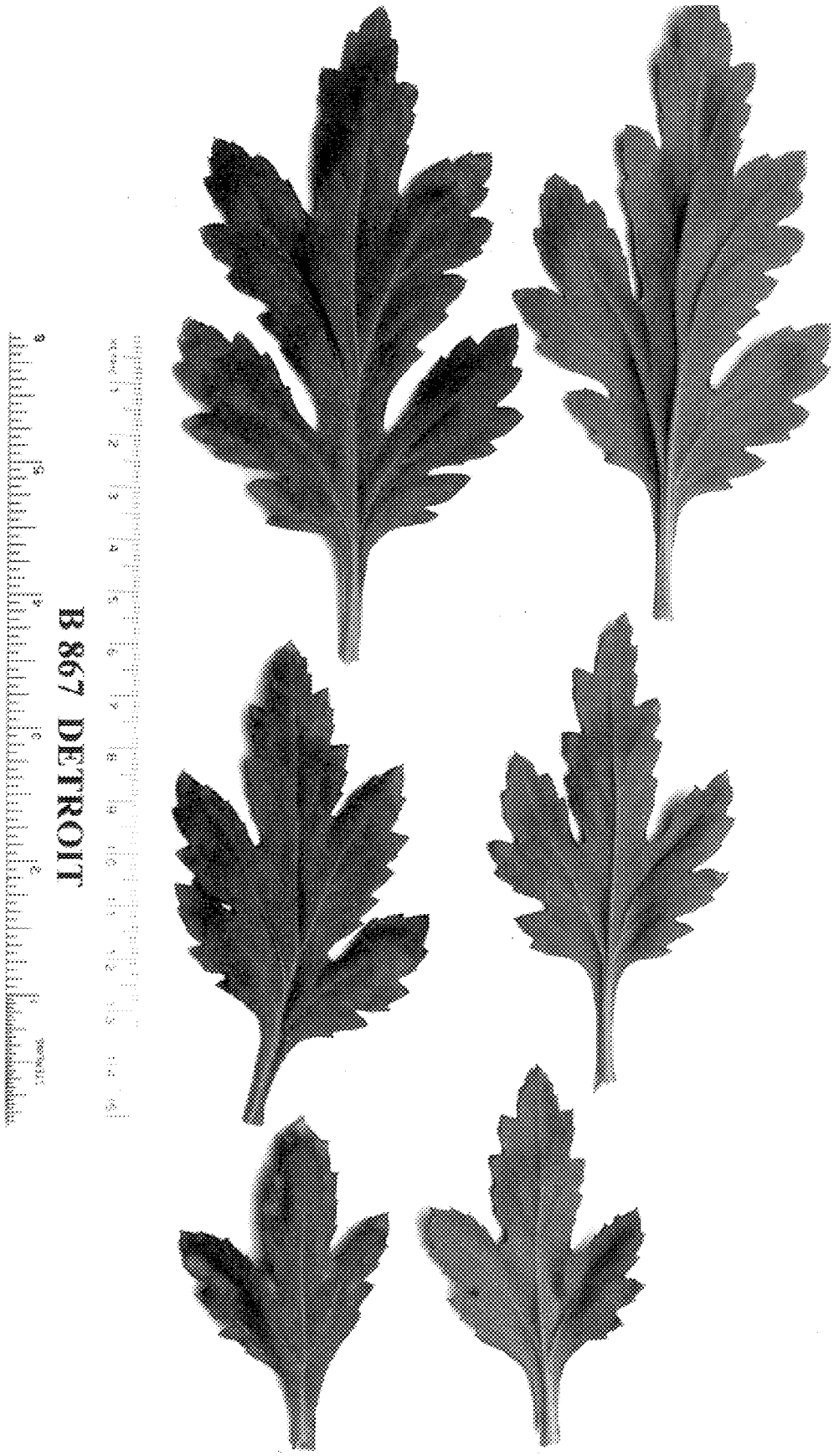
B 867 DETROIT